(12) United States Patent
Goldberg et al.

(10) Patent No.: US 8,920,789 B2
(45) Date of Patent: Dec. 30, 2014

(54) USE OF POLYMER D-LACTIC ACID (PDLA) OR EQUIVALENTS THEREOF TO INHIBIT GROWTH OF CANCER CELLS AND DIAGNOSE CANCERS

(75) Inventors: Joel S. Goldberg, Durham, NC (US); Joe Brice Weinberg, Durham, NC (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/360,567

(22) Filed: Jan. 27, 2012

(65) Prior Publication Data

US 2012/0195850 A1    Aug. 2, 2012

Related U.S. Application Data

(60) Provisional application No. 61/462,103, filed on Jan. 28, 2011.

(51) Int. Cl.
| | | |
|---|---|---|
| G01N 33/566 | (2006.01) | |
| A61K 31/765 | (2006.01) | |
| A61K 31/225 | (2006.01) | |
| C08G 63/06 | (2006.01) | |
| C07C 69/68 | (2006.01) | |
| A61P 35/00 | (2006.01) | |
| C12N 5/09 | (2010.01) | |
| G01N 33/50 | (2006.01) | |
| G01N 33/574 | (2006.01) | |

(52) U.S. Cl.
CPC .......... A61K 31/765 (2013.01); C12N 2533/40 (2013.01); C12N 5/0693 (2013.01); G01N 33/5011 (2013.01); G01N 33/57407 (2013.01)
USPC ........ 424/78.37; 560/180; 514/547; 528/361; 435/375; 435/7.1

(58) Field of Classification Search
USPC ............................................................ 424/78
See application file for complete search history.

(56) References Cited

U.S. PATENT DOCUMENTS 5,766,748 A * 6/1998 Ikado et al. ................... 428/220

OTHER PUBLICATIONS

"PLOS Medicine". "Hypoxia Responses: How Different Cells and Tumors React to Oxygen Shortage", PLOS Medicine, PLoS Med 3(3): e105. Published Jan. 24, 2006.*
"Sonveaux et al." "Targeting lactate-fueled respiration selectively kills hypoxic tumor cells in mice", The Journal of Clinical Investigation, vol. 118, No. 12, pp. 3930-3942. Published Dec. 2008.*

* cited by examiner

*Primary Examiner* — Audrea Buckley
(74) *Attorney, Agent, or Firm* — Adriano & Associates (57) ABSTRACT

The invention provides method for sequestering or trapping L-lactate in or near a tumor cell comprising contacting an isolated polymer of D-lactic acid (PDLA) or an equivalent, derivative or analog thereof with the tumor cell so that the PDLA binds L-lactate in or near the cell and thereby sequestering or trapping L-lactate in or near the tumor cells.

16 Claims, 4 Drawing Sheets
(1 of 4 Drawing Sheet(s) Filed in Color)

USE OF POLYMER D-LACTIC ACID (PDLA) OR EQUIVALENTS THEREOF TO INHIBIT GROWTH OF CANCER CELLS AND DIAGNOSE CANCERS

This patent application claims the benefit of the filing date of U.S. Ser. No. 61/462,103, filed Jan. 28, 2011, the contents of all of which are herein incorporated by reference in their entireties into the present patent application.

Throughout this application various publications are referenced. The disclosures of these publications in their entireties are hereby incorporated by reference into this application in order to more fully describe the state of the art to which this invention pertains.

BACKGROUND OF THE INVENTION

In 1931, Otto Warburg was awarded the Nobel Prize in medicine for his pioneering work demonstrating glycolysis as the primary anaerobic glucose metabolism within cancer cells (Warburg O W F, Negelein E., *J Gen Physiol*. 1927; 8:519-530). Unfortunately, to date, a universal therapy has not emerged from his work. Since that time, it has become apparent that not all cancer cells utilize glycolysis to produce ATP, but some utilize oxidative phosphorylation (Krebs cycle) to generate energy (Seyfried T N, Shelton L M, *Nutr Metab (Lond)*. 2010; 7:7). More specifically, those cells in the interior of a tumor where the oxygen tension is lowest and the milieu more acidotic tend to utilize glycolysis while those cells in the periphery where oxygen tension is higher tend to utilize oxidative phosphorylation (Vaupel P. *Semin Radiat Oncol*. July 2004; 14 (3): 198-206). Glycolysis generates protons that need to be transported out of the cell to avoid acid build up. Many of the hydrogen ions that are transported out of the cell are accompanied by lactate to maintain electrical neutrality. There are other mechanisms exclusive of lactate that generate anions to buffer the acid production of glycolysis. These include metabolism of pyruvate to bicarbonate by hydration of $CO_2$ catalyzed by various carbonic anhydrases and monocarboxylases (Halestrap A P. *UCSD-Nature Molecule Pages*. 29 Oct. 2009:1-20). Decreasing the intracellular lactate concentration may cause cell death from unchecked acidosis. The intracellular pHs of the interior and exterior tumor cells are similar but the extracellular fluid surrounding the inner cells is orders of magnitude more acidic (Gerweck L E, et al, *Mol Cancer Ther*. May 2006; 5(5):1275-1279). It has been shown that a lactate shuttle exists between inner and outer cells where lactate is converted to pyruvate in the outer cells and then metabolized by oxidative phosphorylation to produce ATP to sustain cancer cells (Brooks G A. *J Physiol*. Dec. 1, 2009; 587(Pt 23):5591-5600).

The explanation of which tumor cells utilize glycolysis is more complex than oxygen availability. Rapid rates of energy production require the expedient but inefficient fermentation of glucose if there are insufficient or functionally abnormal mitochondria to process glucose through oxidative phosphorylation (Seyfried T N, Shelton L M. *Nutr Metab (Lond)*. 2010; 7:7). In addition to the metabolic effects of lactate in glycolysis, lactate has also been shown to contribute to tumor cell invasion and increased cell motility (Gatenby R A, et al. *Cancer Res*. May 15, 2006; 66(10):5216-5223).

More recent investigations have tried to separate lactate production from the hypoxic effects on tumor growth by using genetic markers. These studies suggest lactic acidosis may be independent of oxygen tension and may be associated with a more favorable clinical outcome (Chen J L, et al. *PLoS Genet*. December 2008; 4(12):e1000293). If this concept is true, then inactivation or trapping of lactate could worsen clinical outcome.

One major problem associated with present medications that target tumor metabolism is that they also target normal cells. The compositions of the invention solves the problem in the art. The compositions of the invention are tumoricidal and has the advantage that it is less harmful to cells having mitochondria with the capacity to shuttle pyruvate than the subset of cancer cells that exclusively utilize glycolysis.

SUMMARY OF THE INVENTION

The invention provides methods for sequestering or trapping L-lactate in or near a tumor cell comprising contacting an isolated polymer of D-lactic acid (PDLA) or an equivalent, derivative or analog thereof with the tumor cell so that the PDLA binds L-lactate in or near the cell and thereby sequestering or trapping L-lactate in or near the tumor cells.

The invention also provides methods for determining intracellular or extracellular L-lactate levels comprising exposing a PDLA or an equivalent, derivative or analog thereof to or near a cell so as to bind L-lactic acid in or near the cell and thereby forming a complex, wherein the PDLA is labeled, and detecting the complex.

The invention further provides compositions comprising isolated PDLA or an equivalent, derivative or analog thereof having a molecular weight (MW) of less than 500 Daltons, wherein the composition is substantially free of PDLA or an equivalent, derivative or analog thereof having a MW greater than 500 Daltons.

The invention also provides compositions comprising isolated PDLA or an equivalent, derivative or analog thereof having fewer than 12 monomers of D-lactic acid, wherein the composition is substantially free of PDLA or an equivalent, derivative or analog thereof having more than 12 monomers of D-lactic acid.

The invention also provides kits for sequestering, depleting, measuring, or detecting L-lactic acid in solution, in cell culture, in serum, in a cell, or in an animal comprising isolated PDLA or an equivalent, derivative or analog thereof either unmodified or modified.

The invention also provides methods for treating a cancer comprising administering to a subject an isolated PDLA or an equivalent, derivative or analog thereof under sufficient conditions so as to inhibit tumor cells in the subject thereby treating the subject having a cancer.

The invention further provides methods for preventing cancer by sequestering or trapping L-lactate comprising administering to a subject an isolated PDLA or an equivalent, derivative or analog thereof in an amount effective to sequester or trap L-lactate so as to prevent cancer in the subject.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2. Interaction of D-lactic acid or L-lactic acid with poly-D-lactic acid. The plots show absorption (uV; Y axis), and retention time (min; X axis). Frame 1, D-lactic acid alone; Frame 2, Poly-D-lactic acid alone; Frame 3, D-lactic acid plus poly-D-lactic acid; Frame 4, L-lactic acid alone; Frame 5, poly-D-lactic acid alone; Frame 6, L-lactic acid plus poly-D-lactic acid. Addition of poly-D-lactic acid (2) to D-lactic acid (1) does not modify the chromatogram of the combination (3). Addition of poly-D-lactic acid (5) to L-lactic acid (4) modifies the chromatogram of the combination (6). This indicates that poly-D-lactic acid binds L-lactic acid but not D-lactic acid.

DETAILED DESCRIPTION OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps e, b, and a, and the order of steps c, a, and b. Unless otherwise indicated, all numbers expressing quantities of ingredients, properties such as molecular weight, reaction conditions, and so forth as used herein, are to be understood as being modified in all instances by the term "about."Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques, Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

As used herein, the terms "subject" and "patient" refer to any animal, such as a mammal. Mammals include but are not limited to, humans, murines, simians, felines, canines, equines, bovines, porcines, ovines, caprines, rabbits, mammalian farm animals, mammalian sport animals, and mammalian pets. In many embodiments, the subject will be humans.

As used herein, the term "isolated" or "purified" in reference to PDLA does not require absolute purity.

PDLA compositions of the invention may be produced by using principles of chemistry or biochemistry.

As used herein, "inhibition" or "treatment" of a cancer means to provide an intervention that ameliorates the symptoms of the cancer, reduces the severity of the cancer, alters the course of disease progression, and/or ameliorates or cures the basic disease problem. For example, treatment of a cancer may be accomplished by sequestering or trapping L-lactate. Inhibition or treatment may be partial or total.

The most effective mode of administration and dosage regimen for the compositions of the invention depends upon the location, extent, or type of the disease being treated, the severity and course of the medical disorder, the subject's health and response to treatment and the judgment of the treating physician. Accordingly, the dosages of the compositions of the invention should be titrated to the individual subject and/or by the specific medical condition or disease.

By way of example, the interrelationship of dosages for animals of various sizes and species and humans based on $mg/m^2$ of surface area is well known. Adjustments in the dosage regimen may be made to optimize suppression or modulation of the cancer e.g., doses may be divided and administered on a daily basis or weekly or biweekly or monthly basis or the dose reduced proportionally depending upon the situation (e.g., several divided doses may be administered daily or proportionally reduced depending on the specific therapeutic situation).

As is well known, the dose of the composition of the invention required to achieve an appropriate clinical outcome may be further reduced with schedule optimization.

As used herein, polymer D-lactic acid (PDLA) is also known as poly((R)-2-Hydroxypropanoic acid), (R)-2-Hydroxypropanoic acid homopolymer, poly((R)-2-Hydroxypropionic acid), poly((R)-ethylidenelactic acid), poly((R)-1-Hydroxyethanecarboxylic acid) or D-lactic acid homopolymer.

Compositions of the Invention

The present invention provides a novel composition comprising isolated PDLA or an equivalent, derivative or analog thereof having a molecular weight (MW) of 500 Daltons or less, wherein the composition is substantially free of PDLA or an equivalent, derivative or analog thereof having a MW greater than 500 Daltons. PDLA or an equivalent, derivative or analog thereof may be in the form of a linear polymer with free hydroxyl group next to an ester group at one end and a free carboxylic acid group at the other end or may be in the form of a circular polymer in which one D-lactic acid residue is joined by an ester bond to an adjacent D-lactic acid residue with no free hydroxyl or carboxylic acid group.

In one embodiment, the composition comprises isolated PDLA or an equivalent, derivative or analog thereof having fewer than 12 monomers of D-lactic acid, wherein the composition is substantially free of PDLA or an equivalent, derivative or analog thereof having more than 12 monomers of D-lactic acid.

In another embodiment, the composition contains isolated PDLA or an equivalent, derivative or analog thereof having 7 monomers of D-lactic acid or fewer. In yet another embodiment, the composition that contains isolated PDLA or an equivalent, derivative or analog thereof that have 7 monomers of D-lactic acid or fewer is substantially free of PDLA or an equivalent, derivative or analog thereof having more than 7 monomers of D-lactic acid.

In a further embodiment, the composition contains isolated PDLA or an equivalent, derivative or analog thereof that have between 2 to 4 monomers of D-lactic acid. In yet another embodiment, the composition that contains isolated PDLA or an equivalent, derivative or analog thereof that have between 2 to 4 monomers of D-lactic acid is substantially free of PDLA or an equivalent, derivative or analog thereof having fewer than 2 monomers of D-lactic acid. Additionally, in another embodiment, the composition that contains isolated PDLA or an equivalent, derivative or analog thereof that have between 2 to 4 monomers of D-lactic acid is substantially free of PDLA or an equivalent, derivative or analog thereof having more than 4 monomers of D-lactic acid. Moreover, an additional embodiment provides a composition that contains isolated PDLA or an equivalent, derivative or analog thereof that have between 2 to 4 monomers of D-lactic acid and is substantially free of PDLA or an equivalent, derivative or analog thereof having (1) fewer than 2 monomers of D-lactic acid and (2) more than 4 monomers of D-lactic acid.

Figure 1:
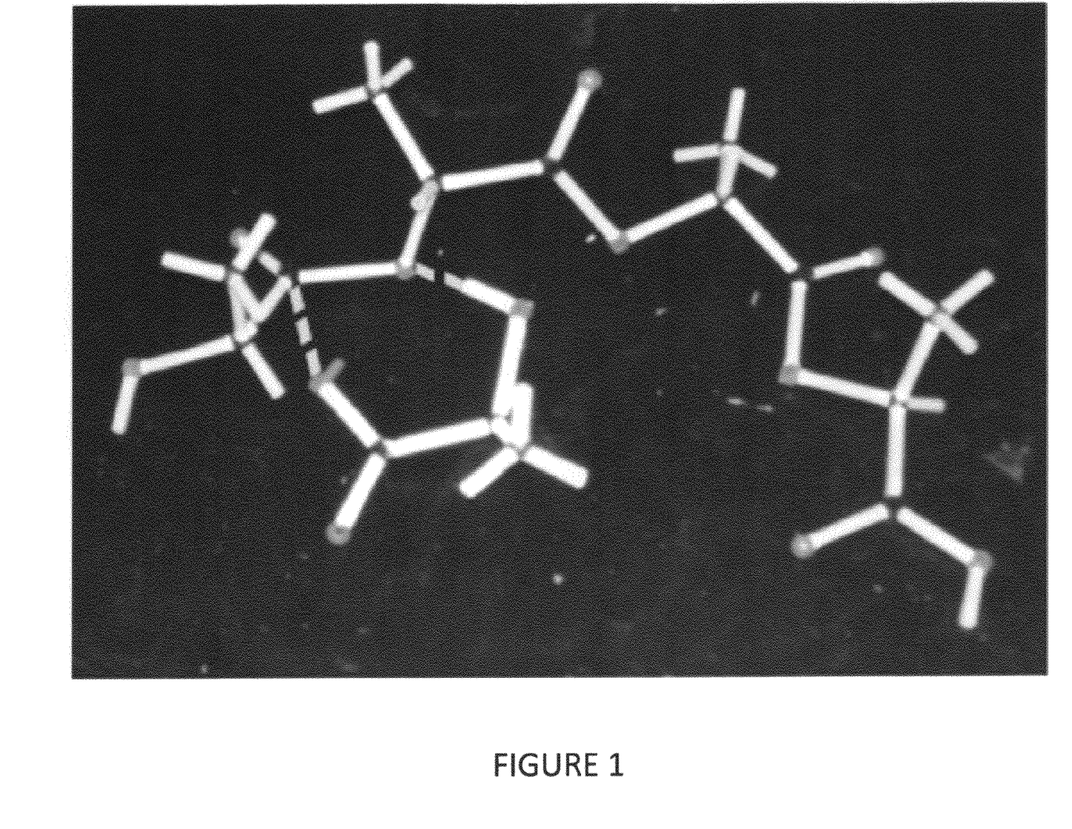
FIG. 1 shows l-lactate (white) binds (yellow) to an isolated PDLA oligomer (green), PDLA oligomer shown is an isolated polymer of four D-lactic acid arising from condensation polymerization involving the hydroxyl group next to the carboxylic acid group of one D-lactic acid residue with the carboxyl group of an adjacent D-lactic acid residue leading to formation of an ester bond and loss of a water molecule. For the PDLA shown, there are three ester bonds and three water molecules lost during condensation polymerization. The orientation of the PDLA shown, where n, the number of D-lactic acid residues, equals 4, has the unreacted hydroxyl group at the left end of the polymer and the unreacted carboxylic acid group at the right end. Although a linear form of PDLA is shown in the figure, PDLA can exist in a circular form with no free hydroxyl or carboxylic acid group but with an ester bond between adjacent D-lactic acid residues.

Polymers of d-lactic acid (PDLA) or an equivalent, derivative or analog thereof may form a stereocomplex (FIG. 1) with l-lactate in solution, in vitro, or in vivo, as in Experiments #1-3, producing lactate deficiency in tumor cells, such as human chronic lymphocytic leukemia (CLL) cells in Experiment #3. Those cancer cells that utilize transport of lactate to maintain electrical neutrality may cease to multiply or die because of lactate trapping, and those cancer cells that benefit from utilization of extracellular lactate may be impaired. Intracellular trapping of lactate may produce a different physiology than inhibition of LDH because the cell loses the option of shuttling pyruvate to an alternative pathway to produce an anion.

Conjugated with stains or fluorescent probes, isolated PDLA or an equivalent, derivative or analog thereof of the invention may be an agent for the diagnosis of tissue lactate and possibly cell differentiation in biopsy specimens. Suitable detectable markers include, but are not limited to, a radioisotope, a fluorescent compound, a bioluminescent compound, chemiluminescent compound, a metal chelator or an enzyme.

Additionally, the PDLA or an equivalent, derivative or analog thereof of the invention may be conjugated to cytotoxic agents. Examples of cytotoxic agents include, but are not limited to ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphtheria toxin, *Pseudamonas exotoxin* (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, maytansinoids, and glucocorticoid and other chemotherapeutic agents, as well as radioisotopes such as $^{212}Bi$, $^{131}I$, $^{131}In$, $^{90}Y$, and $^{186}Re$.

Additional cytotoxic agents include, but are not limited to Dichloroacetate (DCA), 2-deoxyglucose (2-DG) and Lonidamine.

DCA

DCA is a pyruvate dehydrogenase activator, inhibiting the activity of pyruvate dehydrogenase kinase (PDK), and thus promoting the conversion of pyruvate to Acetyl-CoA (Madhok B M, et al. *Br J Cancer*. Jun. 8, 2010; 102(12):1746-1752). Treatment with DCA shifts the fate of pyruvate from glycolysis to mitochondrial oxidative phosphorylation which is likely responsible for its tumoricidal activity. DCA is an inhibitor of all four isoenymes of PDK (Madhok B M, et al. *Br J Cancer*. Jun. 8, 2010; 102(12):1746-1752). DCA has been used for the treatment of congenital and acquired lactic acidosis with the most significant long term side effect of reversible peripheral neuropathy but sedation and elevation of hepatic transaminases have also been reported. The dose required to inhibit colorectal cancer cells in vivo is estimated to be 5-10 times that used in treatment of lactic acidosis (Madhok B M, et al. *Br J Cancer*. Jun. 8, 2010; 102(12):1746-1752; Papandreou I, et al. *Int J Cancer*. Oct. 18, 2010). Potential serum therapeutic doses could be between 20 and 50 mmole/L (Madhok B M, et al. *Br J Cancer*. Jun. 8, 2010; 102(12):1746-1752). In a number of studies, DCA has been shown to be a tumoricidal agent and has reduced lactate levels in growth media in a dose-dependent manner (Michelakis E D, et al. *Sci Transl Med*, May 12, 2010; 2(31):31ra34). Some favorable results have been reported in five patients suffering from glioblastoma multiforme where DCA was used in combination with surgery, temozolomide and radiation (Papandreou I, et al. *Int J Cancer*, Oct. 18, 2010).

2-DG

2-DG is a glucose analog that is a competitive inhibitor of glucose. It is actively transported into cells and phosphorylated into 2-DC phosphate (2-DC-P) by hexokinase (Michelakis E D, et al. *Sci Transl Med*. May 12, 2010; 2(31):31ra34). Further metabolism of 2-DC-P is not possible and thus glycolysis is limited. 2-DC also has additional effects on protein glycosylation separate from its effects on glycolysis and it may enhance radionuclide cytotoxicity (Dwarakanath B S. *J Cancer Res Ther*. September 2009; 5 Suppl 1:527-31; Shrivastava V, et al. *J Cancer Res Ther*. April-June 2006; 2(2):57-64; Raiser M, et al. *Proc Natl Acad Sci USA*. Nov. 18, 2008; 105(46):17807-17811). In vivo studies (in mice) have shown that 2-DG is synergistic with adriamycin and paclitaxel in transplanted human osteosarcoma and non-small cell lung cancer (Pelican H, et al., *Oncogene*. Aug. 7, 2006; 25(34):4633-4646; Prasanna V K, et al. *J Cancer Res Ther*. September 2009; 5 Suppl 1:S44-47). Combination chemotherapy with 2-DG has been trialed in patients with glioblastoma (Prasanna V K, et al. *J Cancer Res Ther*. September 2009; 5 Suppl 1:844-47). Because 2-DG is an analog of glucose it produces actions and side effects in cancer and non-cancer cells. 2-DG may have proconvulsant actions (Gasior M, et al. *Epilepsia. August* 2010; 51(8):1385-1394).

Lonidamine

Lonidamine, a derivative of indazole-3-carboxylic acid is an inhibitor of oxygen consumption and suppresses glycolysis in cancer cells probably through hexokinase suppression (Pelicano H, et al. *Oncogene*. Aug. 7, 2006; 25(34):4633-4646). Its action is non-selective, but synergistic with other chemotherapeutic agents and it has been used in clinical trials for breast, ovarian, lung and glial cancers (Pelicano H, et al., *Oncogene. Aug.* 7, 2006; 25(34):4633-4646). The major complication observed in more than a majority of patients was myalgia that required lowering the dose (Evans W K, et al. *Oncology*. 1984; 41 Suppl 1:69-77).

Other metabolic chemotherapeutic agents that may be conjugated to the isolated PDLA of the compositions of the invention may include: 3-bromopyruvate, an inhibitor of hexokinase, oxythiamine, an inhibitor of transketolase and pyruvate dehydrogenase, and 6-aminonicotinamide, an inhibitor of the pentose phosphate pathway (Pelican H, et al. *Oncogene*. Aug. 7, 2006; 25(34):4633-4646; Gatenby R A, Gillies R J. *Int J Biochem Cell Biol*. 2007; 39(7-8): 1358-1366).

Compositions herein may comprise one or more PDLA oligomers provided herein. The compositions are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compositions described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The PDLA of the compositions of the invention may be derivatized prior to formulation, as described above. The concentrations of the PDLA oligomers in the compositions are effective for delivery of an amount, upon administration, that treats, prevents, or ameliorates one or more of the symptoms of diseases or disorders to be treated.

In one embodiment, the compositions are formulated for single dosage administration.

The composition may be included in a pharmaceutically acceptable carrier in an amount sufficient to exert a therapeutically useful effect in the absence of undesirable side effects on the patient treated. The therapeutically effective concentration may be determined empirically by testing the compositions in in vitro systems described herein, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compositions and derivatives thereof may be, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active composition sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active composition as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

A. Compositions for Oral Administration

Oral pharmaceutical dosage forms are either solid, gel or liquid. The solid dosage forms may be tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crossearmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The composition of the invention may further include agents that protect it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are known. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells.

B. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a composition provided herein may be dispersed e.g., in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinyl alcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80

(TWEEN™ 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intra-arterial infusion of a sterile aqueous solution containing an active compound is an effective mode of administration. Another embodiment is a sterile aqueous or oily solution or suspension containing an active material injected as necessary to produce the desired pharmacological effect.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art.

E. Combination Therapy

In another embodiment, the compositions may be administered in combination, or sequentially, with another therapeutic agent. Such other therapeutic agents include those known for treatment, prevention, or amelioration of one or more symptoms of amyloidosis and neurodegenerative diseases and disorders.

Methods of the Invention

The invention additionally provides method for sequestering or trapping L-lactate in or near a tumor cell. In one embodiment, the method comprises contacting an isolated PDLA or a variant, derivative or analog thereof or any of the compositions of the invention described herein with the tumor cell so that the PDLA binds L-lactate in or near the cell and thereby sequestering or trapping L-lactate in or near the tumor cells.

The invention also provides methods for inhibiting tumor cells by sequestering or trapping L-lactate in the tumor cell by contacting an isolated PDLA or a variant, derivative or analog thereof (or any of the compositions of the invention described herewith) with the tumor cell so that the PDLA binds L-lactate in or near the cell. Additionally, the invention provides methods for killing or inhibiting cancer by sequestering or trapping L-lactate in the tumor cell by contacting an isolated PDLA or a variant, derivative or analog thereof (or any compositions of the invention described herein) with the tumor cell so that the PDLA binds L-lactate in or near the cell. The PDLA or a variant, derivative or analog thereof (or any of the compositions described herein) may be modified to be resistant to esterases.

In accordance with the practice of the invention, the PDLA or a variant, derivative or analog thereof (including in any of the compositions of the invention described herein) may be conjugated to a soluble molecule. Examples of soluble molecules include but are not limited to a dextran, polyethylene glycol, and dendrimer. Additionally, the PDLA or a variant, derivative or analog thereof (including in any of the compositions of the invention described herein) may be conjugated with a therapeutic, detectable, or imaging agent.

Further, the invention provides methods for determining intracellular or extracellular L-lactate levels. In one embodiment, the method comprises exposing PDLA or a variant, derivative or analog thereof (or any compositions of the invention described herein) to or near a cell so as to bind L-lactic acid in or near the cell and thereby forming a complex. The PDLA or a variant, derivative or analog thereof (or any of the compositions of the invention described herein) may be labeled; and so that the complex is detected.

In accordance with the practice of the invention, the PDLA or a variant, derivative or analog thereof (including in any of the compositions of the invention described herein) may be labeled with a radioactive isotope, a fluorescent dye or a calorimetric agent.

In an embodiment of the invention, the method of detection may be effected by fluorescence resonance energy transfer (FRET). In this example, the fluorescent dye may be chemical compounds, such as fluorescein and rhodamine or Cy3™ and Cy5™, or a fluorescent protein such as the green fluorescent protein (GFP) and mutants or derivatives thereof, such as ECFP or EYFP.

In an embodiment of the invention, the method of detection may be effected by detection of a pronounced fluorescence upon binding of L-lactic acid by PDLA or a variant, derivative or analog thereof (including in any of the compositions of the invention described herein) labeled with a fluorescent dye (e.g., Oregon Green™ 488-X, 6-FAM™, TET™, Cy3™, Rhodamine Red®-X, TAMRA™, ROX™, Bodipy 630/650™-X, Bodipy 650/665™-X, and Cy5™) and a fluorescent dye quencher (e.g., Dabcyl, BHQ™-1, BHQ™-2, and Iowa Black™ FQ/RQ) or a pair of fluorescent dyes that can interact in fluorescence resonance energy transfer. For example, presence of one fluorescent dye on one end of PDLA or a variant, derivative or analog thereof (including in any of the compositions of the invention described herein) and a quencher or its FRET pair on the other end produces a notable difference in the emission fluorescence spectrum (either wavelength or amplitude) in the absence or presence of L-lactic acid. A change in the emission fluorescence spectrum is produced upon binding to L-lactic acid as the distance and orientation of the two labeled dyes are changed.

The invention further provides methods for treating a cancer comprising administering to a subject an isolated PDLA or a variant, derivative or analog thereof (or any of the compositions of the invention described herein) under sufficient conditions so as to inhibit tumor cells.

Examples of cancers include but are not limited to colorectal cancer, osteosarcoma, non-small cell lung cancer, breast cancer, ovarian cancer, glial cancer, solid tumors, metastatic tumor, acute lymphoblastic leukemia, acute myelogenous leukemia, adrenocortical carcinoma, Kaposi sarcoma, lymphoma, anal cancer, astrocytomas, basal cell carcinoma, bile duct cancer, bladder cancer, bone cancer, brain tumor, breast cancer, bronchial tumor, cervical cancer, chronic lymphocytic leukemia, chronic myelogenous leukemia, chronic myeloproliferative disorders, colon cancer, colorectal cancers, ductal carcinoma in situ, endometrial cancer, esophageal cancer, eye cancer, intraocular, retinoblastoma, metastatic melanoma, gallbladder cancer, gastric cancer, gastrointestinal carcinoid tumor, gastrointestinal stromal tumors, glioblastoma, glioma, hairy cell leukemia, head and neck cancer, hepatocellular carcinoma, hepatoma, Hodgkin lymphoma, hypopharyngeal cancer, Langerhans cell histiocytosis, laryngeal cancer, lip and oral cavity cancer, liver cancer, lobular carcinoma in situ, lung cancer, non-small cell lung cancer, small cell lung cancer, lymphoma, AIDS-related lymphoma, Burkitt lymphoma, non-Hodgkin lymphoma, cutaneous T-cell lymphoma, melanoma, squamous neck cancer, mouth cancer, multiple myeloma, myelodysplastic syndromes, myelodysplastic/myeloproliferative neoplasms, nasal cavity and paranasal sinus cancer, nasopharyngeal cancer, neuroblastoma, oral cavity cancer, oropharyngeal cancer, osteosarcoma, ovarian cancer, pancreatic carcinoma, papillary carcinomas, parathyroid cancer, penile cancer, pharyngeal cancer, pheochromocytoma, pineal parenchymal tumors, pineoblastoma, pituitary tumor, pleuropulmonary blastoma, primary central nervous system lymphoma, prostate cancer, rectal cancer, renal cell cancer, salivary gland cancer, sarcoma, Ewing sarcoma, soft tissue sarcoma, squamous cell carcinoma, Sezary syndrome, skin cancer, Merkel cell carcinoma, testicular cancer, throat cancer, thymoma, thymic carcinoma, thyroid cancer, urethral cancer, endometrial cancer, uterine cancer, uterine sarcoma, vaginal cancer, vulvar cancer, Waldenstrom macroglobulinemia, and Wilms tumor.

The invention also provides for methods for preventing cancer by sequestering or trapping L-lactate in an effective amount comprising administering to a subject an isolated PDLA or a variant, derivative or analog thereof (or any of the compositions of the invention described herein) under sufficient conditions so as to prevent the cancer.

Kits

According to another aspect of the invention, kits are provided. For example, the invention provides kits for sequestering, depleting, measuring, or detecting L-lactic acid in solution, in cell culture, in serum, in a cell, or in an animal comprising isolated PDLA or a variant, derivative or analog thereof (or any of the compositions of the invention described herein) of the invention either unmodified or modified. For example, isolated PDLA may be used free in solution or conjugated to a solid support to deplete lactic acid produced during fermentation, such as in beer and wine manufacturing process. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but may be attached to the outside of the package, for example, pipettes.

Kits may optionally contain instructions for administering the compositions of the invention to a subject having a condition in need of treatment. Kits may also comprise instructions for approved uses of compounds herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In still other embodiments, compositions are provided in a polymeric matrix or in the form of a liposome.

The following examples are provided to further illustrate aspects of the invention. These examples are non-limiting and should not be construed as limiting any aspect of the invention.

EXAMPLES

PDLA Interferes with l-lactate Measurement
(Methods and Results)

Experiment #1

Forty mg of d-lactic acid (Sigma-Aldrich, St. Louis, Mo.; catalog no. L0625) was polymerized in a microwave oven according to the method of Pandey and Aswath (*J Biomater Sci Polym Ed.* 2009; 20(1):33-48). Briefly, d-lactic acid was transferred to 2 ml Reacti-Vials (Pierce Chemical Co., Rockford, Ill.) and the polymerization was carried out vented in a GE Spacemaker Model JVM 1650WH05 (Serial #900524B;

manufactured April 2006) with an RF output frequency of 2450 MHz in the absence of any added solvent or catalyst. Polymerization was carried out starting at Power 1 setting on the microwave and weighing at 30 second intervals. Power setting was increased stepwise until about Power 4 which resulted in a sample weight of 20 mg corresponding to 50% weight loss. Weight loss was from water during polymer esterification and dehydration. During the course of the microwave process, d-lactic acid crystals undergo a state change from a solid to a liquid and then to a gel at the end of the process. Similar procedure was used to produce PLLA with l-lactic acid.

The polymerization process may be monitored by taking samples during the course of the microwave treatment and analyzed by Fourier transform infrared (FT-IR) spectroscopy, proton nuclear magnetic resonance (1H-NMR) spectroscopy and/or gel-permeation chromatograph (GPC). The final synthesized PDLA or PLLA may be further purified or isolated to obtain the desired molecular weight or number of lactic acid residues in the oligomer by gel-permeation chromatography, as described in Pandey and Aswath (*J Biomater Sci Polym Ed*. 2009; 20(1):33-48).

In normal saline, at a temperature of 37 degrees centigrade, a control solution of 1 ml of l-lactic acid (50 mg/L) (Sigma) and separately 1 ml of an experimental solution of 1 ml of 50 mg/L of l-lactic acid with 20 mg of PDLA were incubated for 2 hours. Measurement of l-lactate with L-Lactate Accuvin Test strips (Accuvin LLC, Napa, Ca), using stereospecific lactate dehydrogenase and a tetrazolium color indicator, measured less l-lactate (interference) in the experimental sample as evidenced by colorimetric determination. Experimental sample vs. control measured 10 mg/L vs. 50 mg/L of l-lactate. Other relevant tests using similar methodology and D-Lactate Accuvin Test strips are as follows:
1. Interference when Polymer L-Lactate (PLLA) (100 mg) was added to a 1 ml solution of 800 mg/L d-lactic acid.
2. No interference when 50 mg/L l-lactic acid solution was added to a 60 mg/L d-lactic acid solution. (Table 1.)

TABLE 1

Interference reactions of PDLA and l-lactate & PLLA and d-lactate in saline

|  | l-lactate test strip | d-lactate test strip |
|---|---|---|
| l-lactic acid (0.05 mg) | 50 mg/L |  |
| l-lactic acid (0.05 mg) + PDLA (20 mg) | 10 mg/L |  |
| d-lactic (0.8 mg) |  | 800 mg/L |
| d-lactic (0.8 mg) acid + PLLA (100 mg) |  | not detected |
| d-lactic (0.05 mg) acid + l-lactic acid (0.06 mg) | 50 mg/L |  |

Conclusion of experiment #1: PDLA in normal saline solution decreases the measurement of l-lactate in normal saline solution and PLLA in normal saline solution decreases the measurement of d-lactate in normal saline solution.

Experiment #2

After approval from the director of the clinical laboratory and the chairman of the human studies committee of the Durham Veterans Affairs Medical Center and after vigorous exercise, 18 ml of blood was drawn from a human subject. The blood was collected in three vials each containing sodium fluoride/potassium oxalate. Tubes 1 and 3 were centrifuged at 3400 rpm for 15 minutes and the serum was frozen. To tube 2 was added and mixed 0.5 ml of a 1 ml normal saline solution containing a mixture of PDLA d-lactate oligomers with an initial weight of 100 mg of d-lactic acid that had been microwave polymerized with loss of 30 mg of water. Tube 2 was then centrifuged at 3400 rpm and the serum was frozen. Tubes 1-3 containing serum were frozen at −5 degrees centigrade for 12 hours and then defrosted in an incubator at 37 degrees centigrade for 3 hours prior to assay. The tubes were then placed on ice and processed in the laboratory.

Serum was processed using the Siemens Dimension Vista System Flex reagent cartridge at the Durham Veterans Affairs Medical Center. Reference values of l-lactate are in the range of 0.4-2.0 mmol/L (Table 2.)

TABLE 2

PDLA decreases measurement of l-lactate in blood

| Tube | l-lactate conc. | PDLA | l-lactate conc. with dilution |
|---|---|---|---|
| 1 | 9.1 mmol/L | 0 | 9.1 mmol/L |
| 2 | 7.0 mmol/L | 0.5 ml | 7.58 mmol/L |
| 3 | 8.6 mmol/L | 0 | 8.6 mmol/L |

Conclusion of experiment #2: PDLA of unknown molecular weight oligomers reduces the measurement of l-lactate in blood samples without addition of catalyst or heat.
Proposed Reaction

*l*-lactate+PDLA=PDLA~*l*-lactate complex+PDLA+*l*-lactate

Experiment #3

To determine the ability of PDLA and PLLA to mediate cytotoxicity for malignant cells, freshly isolated human chronic lymphocytic leukemia (CLL) cells were cultured with the agents for 72 hours at 37° C. in 5% carbon dioxide/95% air using SFM™ tissue culture medium (Invitrogen, Carlsbad, Calif.). The cells were cultured in triplicate with eight 2-fold dilutions of the agents (from 2.000 to 0.016 mg/mL). Cytotoxicity was determined with an assay using the tetrazolium-based compound MTS (Promega, Madison, Wis.) (Levesque M C, et al. *Leukemia. February* 2003; 17(2): 442-450).

Conclusion of experiment #3: The studies demonstrated cytotoxicity for the CLL cells, with the mean effective dose for 50% cytotoxic effect of 1.30 mg/mL for PDLA (1.93 and 0.66 mg/mL in patients A and B), and 2.14 mg/mL for PLLA (2.65 and 1.63 mg/mL in patients A and B). Thus, the PDLA was effective at a lower concentration than PLLA.
Stereocomplex Model of PDLA and l-Lactate The beta helix strand formed by PDLA oligomers could template for l-lactate because the lactate anion is attracted to the carbonyl of the ester which carries a partial positive charge because of the inductive effects of the adjacent oxygen molecules. Hydrogen bonding could exist between the OH group of l-lactate and the ester oxygen of oligomers of PDLA. With these attractions, the methyl groups of PLDA and lactate are favorably oriented with minimal steric effects. This complex which has been more specifically named a homo-stereocomplex is probably distinct from the stereo PLDA~PLLA complex. The minimum size oligomer of PDLA that would be needed to complex intracellular l-lactate may be less than 500 Daltons. (FIG. 1)
Discussion of Experimental Section The experimental section supports that PDLA oligomers form a stereocomplex with l-lactate. The reaction occurs spontaneously in both normal saline and plasma (delta G negative and $K_{equilibrium}$ greater than 1). Separation of the polymer to oligomers less than 500 Daltons (231, 308, 385 or 462 corresponding to 3×, 4×, 5×, or 6× d-lactate monomers respectively) may be the ideal weights for biologic application assuming that rapid plasma hydrolysis does not occur in vivo and multiple binding sites exist for l-lactate to complex with PDLA oligomers. (Table 3.)

TABLE 3

PDLA oligomer weights and hydrogen bond acceptors and donors

| # of d-lactate monomers | Molecular weight | Hydrogen bond acceptors | Hydrogen bond donors |
|---|---|---|---|
| 2 | 154 | 5 | 0-2 |
| 3 | 231 | 7 | 0-2 |
| 4 | 308 | 9 | 0-2 |
| 5 | 385 | 11 | 0-2 |
| 6 | 462 | 13 | 0-2 |

Estimation of Three Compartment (Blood, Extracellular Tumor, Intracellular Tumor) PDLA Concentrations The size, charge and lipophilic properties of the PDLA oligomers will mostly determine the likelihood that it will be available in the extracellular space to complex l-lactate. Using control values of pHe=6.77 (extracellular pH) and pHp=7.4 (plasma pH), assuming no active transport, the ion distribution of PDLA with a pKa 3.86 would be approximately (Gerweck L E, et al. *Mol Cancer Ther*. May 2006; 5(5):1275-1279):

$pHp = 3.86 + \log [PDLA_p^-]/[PDLA_p]$ {capillary}
$pH_e = 3.86 + \log [PDLA_e^-]/[PDLA_e]$
$3.54 = \log [PDLA_p^-]/[PDLA_p]$ {capillary} $2.91 = \log [PDLA_e^-]/[PDLA_e]$
Antilog of equations
$3470 = [PDLA_p^-]/[PDLA_p]$ {capillary} $2042 = [PDLA_e^-]/[PDLA_e]$
$[PDLA_p] \sim [PDLA_e]$ (Assuming equilibrium across the capillary)
$[PDLA_p^-]/[PDLA_e^-] = 3470/2042 = 1.70$ Thus the approximate plasma concentration of the anion oligomer would be 1.70× that of the extracellular concentration.

The size, charge and lipophilic properties of the oligomer will mostly determine the likelihood that it will be available in the cytosol to complex l-lactate. However, the acid milieu of the extracellular compartment surrounding the tumor will aid in intracellular ion trapping of PDLA. Using control values of pHe=6.77 (extracellular pH) and pH i=7.17 (intracellular pH), assuming no active transport, the effects of intracellular ion trapping of PDLA with a pKa 3.86 would be approximately (Gerweck L E, et al, *Mol Cancer Ther*. May 2006; 5(5):1275-1279):

$pH_e = 3.86 + \log [PDLA_e^-]/[PDLA_e]$ {cell wall} $pH_i = 3.86 + \log [PDLA_i^-]/[PDLA_i]$
$2.91 = \log [PDLA_e^-]/[PDLA_e]$ {cell wall} $3.31 = \log [PDLA_i^-]/[PDLA_i]$
Antilog of equations
$2042 = [PDLA_e^-]/[PDLA_e]$ {cell wall} $813 = [PDLA_i^-]/[PDLA_i]$
$[PDLA_e] \sim [PDLA_i]$ (Assuming equilibrium across the cell wall)
$[PDLA_e^-]/[PDLA_i^-] = 2041/813 = 2.51$ Thus the approximate intracellular concentration of the anion oligomer would be 2.51× that of the extracellular concentration. The $[PDLA_p^-]/[PDLA_i^-]=0.68$ (plasma concentration to intracellular concentration). Lactate concentration in some aggressive cancers may range between 10-12.9 micromoles/gm (Walenta S, et al. *Cancer Res*. Feb. 15, 2000; 60(4):916-921; Brizel D M, et al. *Int J Radial Oncol Biol Phys*. Oct. 1, 2001; 51(2):349-353),

REFERENCES

1. Warburg O W F, Negelein E., The Metabolism of Tumors in the Body. *J Gen Physiol*. 1927; 8:519-530.
2. Seyfried T N, Shelton L M. Cancer as a metabolic disease. *Nutr Metab (Lond)*. 2010; 7:7.
3. Vaupel P. Tumor microenvironmental physiology and its implications for radiation oncology, *Semin Radiat. Oncol*. July 2004; 14(3):198-206.
4. Halestrap A P. Monocarbgoxylate transporter 1. *UCSD-Nature Molecule Pages*. 29 Oct. 2009:1-20.
5. Gerweck L E, Vijayappa S, Kozin S. Tumor pH controls the in vivo efficacy of weak acid and base chemotherapeutics. *Mol Cancer Ther*. May 2006; 5(5):1275-1279.
6. Brooks G A. Cell-cell and intracellular lactate shuttles. *J Physiol*. Dec. 1, 2009; 587(Pt 23):5591-5600.
7. Gatenby R A, Gawlinski E T, Gmitro A F, Kaylor B, Gillies R J. Acid-mediated tumor invasion: a multidisciplinary study. *Cancer Res*. May 15, 2006; 66(10):5216-5223.
8. Chen J L, Lucas J E, Schroeder T, et al. The genomic analysis of lactic acidosis and acidosis response in human cancers. *PLoS Genet*. December 2008; 4(12):e1000293.
9. Madhok B M, Yellin S, Perry S L, Hughes T A, Jayne D G. Dichloroacetate induces apoptosis and cell-cycle arrest in colorectal cancer cells, *Br J Cancer*. Jun. 8, 2010; 102(12): 1746-1752.
10. Papandreou I, Goliasova T, Denko N C. Anti-cancer drugs that target metabolism, is dichloroacetate the new paradigm? *Int J Cancer*. Oct. 18, 2010.
11. Michelakis E D, Sutendra G, Dromparis P, et al. Metabolic modulation of glioblastoma with dichloroacetate, *Sci Transl Med*. May 12, 2010; 2(31):31ra34.
12. Dwarakanath B S. Cytotoxicity, radiosensitization, and chemosensitization of tumor cells by 2-deoxy-D-glucose in vitro. *J Cancer Res Ther*. September 2009; 5 Suppl 1:S27-31.
13. Shrivastava V, Mishra A K, Dwarakanath B S, Ravindranath T. Enhancement of radionuclide induced cytotoxicity by 2-deoxy-D-glucose in human tumor cell lines. *J Cancer Res Ther*. April-June 2006; 2(2):57-64.
14. Raiser M, Wamelink M M, Struys E A, et al. A catabolic block does not sufficiently explain how 2-deoxy-D-glucose inhibits cell growth. *Proc Natl Acad Sci USA*. Nov. 18, 2008; 105(46):17807-17811.
15. Pelicano H, Martin D S, Xu R H, Huang P. Glycolysis inhibition for anticancer treatment. *Oncogene*. Aug. 7, 2006; 25(34):4633-4646.
16. Prasanna V K, Veukataramana N K, Dwarakanath B S, Santhosh V. Differential responses of tumors and normal brain to the combined treatment of 2-DG and radiation in glioablastoma. *J Cancer Res Ther*. September 2009; 5 Suppl 1:S44-47.
17. Gasior M, Yankura J, Hartman A L, French A, Rogawski M A. Anticonvulsant and proconvulsant actions of 2-deoxy-D-glucose. *Epilepsia*. August 2010; 51(8):1385-1394.
18. Evans W K, Shepherd F A, Mullis B. Phase II evaluation of Lonidamine in patients with advanced malignancy. *Oncology*. 1984; 41 Suppl 1:69-77.
19. Gatenby R A, Gillies R J. Glycolysis in cancer: a potential target for therapy, *Int J Biochem Cell Biol*. 2007; 39(7-8): 1358-1366.
20. Ikada Y, Jamshidi, K., Tsuji, H. Hyon, S.-H. *Macromolecules*. 1987; 20:904.

21. Tsuji H. Poly(lactide) stereocomplexes: formation, structure, properties, degradation, and applications. *Macromol Biosci*. Jul. 14, 2005; 5(7):569-597.
22. deJong S J, van Dijik-Wolthuis, W. N. E., Kettenes-van den Bosch, J. J., et al, Monodisperse enantiomeric lactic acid oligomers: Preparation, characterization, and stereocomplex formation. *Macromolecules*. 1998; 31(19):6397-6402.
23. Hennink W E, De Jong S J, Bos G W, Veldhuis T F, van Nostrum C F. Biodegradable dextran hydrogels crosslinked by stereocomplex formation for the controlled release of pharmaceutical proteins. *Int J Pharm*. Jun. 11, 2004; 277(1-2):99-104.
24. Slager J, Domb A J. Biopolymer stereocomplexes. *Adv Drug Deliv Rev*. Apr. 25, 2003; 55(4):549-583.
25. Slager J, Domb A J, Stereocomplexes based on poly(lactic acid) and insulin: formulation and release studies. *Biomaterials*. November 2002; 23(22):4389-4396.
26. Pandey A, Aswath P B. Microwave synthesis of poly(L-lactic acid). *J Biomater Sci Polym Ed*. 2009; 20(0:33-48.
27. Levesque M C, Misukonis M A, O'Loughlin C W, et al, IL-4 and interferon gamma regulate expression of inducible nitric oxide synthase in chronic lymphocytic leukemia cells. *Leukemia*. February 2003; 17(2):442-450.
28. Walenta S, Wetterling M, Lehrke M, et al. High lactate levels predict likelihood of metastases, tumor recurrence, and restricted patient survival in human cervical cancers. *Cancer Res*. Feb. 15, 2000; 60(4):916-921.
29. Brizel D M, Schroeder T, Scher R L, et al. Elevated tumor lactate concentrations predict for an increased risk of metastases in head-and-neck cancer. *Int J Radiat Oncol Biol Phys*. Oct. 1, 2001; 51(2):349-353.
30. Lipinski C A, Lombardo F, Dominy B W, Feeney P. T. Experimental and computational approaches to estimate solubility and permeability in drug discovery and development settings. *Adv Drug Deliv Rev*. Mar. 1, 2001; 46(1-3):3-26.
31. Schwickert G, Walenta S, Sundfor K, Rofstad E K, Mueller-Klieser W. Correlation of high lactate levels in human cervical cancer with incidence of metastasis. *Cancer Res*. Nov. 1, 1995; 55(21):4757-4759.
32. Walenta S, Salameh A, Lyng H, et al. Correlation of high lactate levels in head and neck tumors with incidence of metastasis. *Am J Pathol*. February 1997; 150(2):409-415.
33. Van Tomme S R, Hennink W E. Biodegradable dextran hydrogels for protein delivery applications. *Expert Rev Med Devices*, March 2007; 4(2):147-164.
34. Van Tomme S R, Mens A, van Nostrum C F, Hennink W E. Macroscopic hydrogels by self-assembly of oligolactate-grafted dextran microspheres. *Biomacromolecules*. January 2008; 9(1):158-165.
35. Walenta S, Schroeder T, Mueller-Klieser W. Metabolic mapping with bioluminescence: basic and clinical relevance. *Biomol Eng*. February 2002; 18(6):249-262.
36. Yamagata M, Hasuda K, Stamato T, Tannock I F. The contribution of lactic acid to acidification of tumours: studies of variant cells lacking lactate dehydrogenase. *Br J Cancer*. June 1998; 707(11):1726-1731.
37. Kennedy K M, Dewhirst M W. Tumor metabolism of lactate: the influence and therapeutic potential for MCT and CD147 regulation. *Future Oncol*. January 2010; 6(1):127-148.
38. Izumi H, Torigoe T, Ishiguchi H, et al. Cellular pH regulators: potentially promising molecular targets for cancer chemotherapy. *Cancer Treat Rev*. December 2003; 29(6):541-549.
39. Joukyuu R, Mizuno S, Amakawa T, Tsukada T, Nishina T, Kitamura M. Hereditary complete deficiency of lactate dehydrogenase H-subunit. *Clin Chem*. April 1989; 35(4):687-690.
40. Kanno T, Sudo K, Takeuchi I, et al. Hereditary deficiency of lactate dehydrogenase M-subunit. *Clin Chim Acta. Dec*. 8, 1980; 108(2):267-276.
41. Wakabayashi H, Tsuchiya M, Yoshino K, Kaku K, Shigei H. Hereditary deficiency of lactate dehydrogenase H-subunit. *Intern Med*. July 1996; 35(7):550-554.
42. Tsuji H, Miyauchi S. Enzymatic hydrolysis of poly(lactide)s: effects of molecular weight, L-lactide content, and enantiomeric and diastereoisomeric polymer blending. *Biomacromolecules*. Summer 2001; 2(2):597.604.
43. Tsuji H. In vitro hydrolysis of blends from enantiomeric poly(lactide)s. Part 4: well-homo-crystallized blend and nonblended films. *Biomaterials*. February 2003; 24(4):537-547.
44. Tsuji H, Del Carpio C A. In vitro hydrolysis of blends from enantiomeric poly(lactide)s. 3. Homocrystallized and amorphous blend films. *Biomacromolecules*. January-February 2003; 4(1):7-11.
45. Tsuji H, Ikarashi K. In vitro hydrolysis of poly(L-lactide) crystalline residues as extended-chain crystallites. Part I: long-term hydrolysis in phosphate-buffered solution at 37 degrees C. *Biomaterials*, November 2004; 25(24):5449-5455.
46. Bos G W, Hennink W E, Brouwer L A, et al. Tissue reactions of in situ formed dextran hydrogels crosslinked by stereocomplex formation after subcutaneous implantation in rats. *Biomaterials*. June 2005; 26(18):3901-3909.
47. Slager J, Domb A J. Hetero-stereocomplexes of D-poly (lactic acid) and the LHRH analogue leuprolide. Application in controlled release. *Eur J Pharm Biopharm*. November 2004; 58(3):461-469.
48. Stenekes R J, Loebis A E, Fernandes C M, Crommelin D J, Hennink W E. Controlled release of liposomes from biodegradable dextran microspheres: a novel delivery concept. *Pharm Res*. June 2000; 17(6):690-695.
49. Panyam J, Labhasetwar V. Targeting intracellular targets. *Curr Drug Deliv*. July 2004; 1(3):235-247.
50. Petersen C. D-lactic acidosis. *Nutr Clin Pract*. December 2005; 20(6):634-645.
51. Uribarri I, Oh M S, Carroll H J. D-lactic acidosis. A review of clinical presentation, biochemical features, and pathophysiologic mechanisms. *Medicine (Baltimore)*. March 1998; 77(2):73-82.

What is claimed is:

1. A method for sequestering or trapping L-lactate in or near a tumor cell comprising contacting an isolated polymer of D-lactic acid (PDLA) or an equivalent, derivative or analog thereof with the tumor cell,
   wherein the isolated PDLA equivalent, derivative or analog comprises fewer than 12 monomers of D-lactic acid forming a beta helix strand comprising a carbonyl ester with a partial positive charge attracted to lactate anion, an ester oxygen formed hydrogen bond with OH group of L-lactate, and methyl groups oriented favorable relative to a methyl group of L-lactate, so that the isolated PDLA or an equivalent, derivative or analog binds L-lactate in or near the cell, thereby sequestering or trapping L-lactate in or near the tumor cells.

2. A method for inhibiting tumor cells by sequestering or trapping L-lactate in the tumor cell by the method of claim 1.

3. The method of claim 1, wherein the PDLA or an equivalent, derivative or analog thereof is conjugated to a molecule that is soluble in bodily fluids or aqueous solutions.

4. The method of claim 3, wherein the soluble molecule is a dextran, polyethylene glycol, or dendrimer.

5. A method for inhibiting cancer cells in a subject by sequestering or trapping L-lactate in the tumor cell by the method of claim 1.

6. The method of claim 1, wherein the PDLA or an equivalent, derivative or analog thereof is modified to be resistant to esterases.

7. The method of claim 1, wherein the PDLA or an equivalent, derivative or analog thereof is conjugated with a therapeutic, detectable, or imaging agent.

8. A method for treating a cancer associated with increased dependence on glycolysis for ATP production or increased dependence on cellular uptake of L-lactate as an energy source comprising administering to a subject an isolated PDLA or an equivalent, derivative or analog thereof under sufficient conditions to sequester or trap L-lactate in or near tumor cells so as to inhibit tumor cells in the subject, wherein the isolated PDLA equivalent, derivative or analog comprises fewer than 12 monomers of D-lactic acid forming a beta helix strand comprising a carbonyl ester with a partial positive charge attracted to lactate anion, an ester oxygen formed hydrogen bond with OH group of L-lactate, and methyl groups oriented favorable relative to a methyl group of L-lactate, thereby treating the subject having a cancer.

9. The method of claim 8, wherein the cancer associated with increased dependence on glycolysis for ATP production or increased dependence on cellular uptake of L-lactate as an energy source is selected from the group consisting of colorectal cancer, osteosarcoma, non-small cell lung cancer, breast cancer, ovarian cancer and glial cancer.

10. A method for sequestering or trapping L-lactate in or near a tumor cell comprising contacting a composition comprising isolated PDLA or an equivalent, derivative or analog thereof having fewer than 12 monomers of D-lactic acid, wherein the isolated PDLA or an equivalent, derivative or analog comprises a beta helix strand comprising a carbonyl ester with a partial positive charge attracted to lactate anion, an ester oxygen formed hydrogen bond with OH group of L-lactate, and methyl groups oriented favorable relative to a methyl group of L-lactate with the tumor cell so that the PDLA or an equivalent, derivative or analog thereof of the composition binds L-lactate in or near the cell, thereby sequestering or trapping L-lactate in or near the tumor cells.

11. A method for inhibiting tumor cells associated with increased dependence on glycolysis for ATP production or increased dependence on cellular uptake of L-lactate as an energy source by sequestering or trapping L-lactate in or near the tumor cell by the method of claim 10.

12. The method of claim 10, wherein the PDLA or an equivalent, derivative or analog thereof is conjugated to a molecule that is soluble in bodily fluids or aqueous solutions.

13. A method for inhibiting cancer cells associated with increased dependence on glycolysis for ATP production or increased dependence on cellular uptake of L-lactate as an energy source in a subject by sequestering or trapping L-lactate in or near the tumor cell by the method of claim 10.

14. The method of claim 10, wherein the PDLA or an equivalent, derivative or analog thereof of the composition is modified to be resistant to esterases.

15. The method of claim 10, wherein the PDLA or an equivalent, derivative or analog thereof is conjugated with a therapeutic, detectable, or imaging agent.

16. A method for treating a cancer associated with increased dependence on glycolysis for ATP production or increased dependence on cellular uptake of L-lactate as an energy source comprising administering to a subject a composition comprising isolated PDLA or an equivalent, derivative or analog thereof having fewer than 12 monomers of D-lactic acid, wherein the isolated PDLA equivalent, derivative or analog comprises a beta helix strand comprising a carbonyl ester with a partial positive charge attracted to lactate anion, an ester oxygen formed hydrogen bond with OH group of L-lactate, and methyl groups oriented favorable relative to a methyl group of L-lactate under sufficient conditions to sequester or trap L-lactate in or near tumor cells so as to inhibit tumor cells in a subject thereby treating a subject having a cancer.

\* \* \* \* \*